(12) United States Patent
Bohlmann et al.

(10) Patent No.: US 7,906,533 B2
(45) Date of Patent: Mar. 15, 2011

(54) NICOTINAMIDE PYRIDINUREAS AS VASCULAR ENDOTHELIAL GROWTH FACTOR (VEGF) RECEPTOR KINASE INHIBITORS

(75) Inventors: Rolf Bohlmann, Berlin (DE); Martin Haberey, Berlin (DE); Andreas Huth, Berlin (DE); Stuart Ince, Berlin (DE); Martin Krueger, Berlin (DE); Karl-Heinz Thierauch, Berlin (DE); Holger Hess-Stumpp, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 1233 days.

(21) Appl. No.: 11/262,953

(22) Filed: Nov. 1, 2005

(65) Prior Publication Data

US 2006/0160861 A1 Jul. 20, 2006

Related U.S. Application Data

(60) Provisional application No. 60/626,914, filed on Nov. 12, 2004.

(30) Foreign Application Priority Data

Nov. 3, 2004 (EP) .................................. 04090420

(51) Int. Cl.
*A61K 31/4439* (2006.01)
*C07D 401/14* (2006.01)

(52) U.S. Cl. ........................................ 514/333; 546/256
(58) Field of Classification Search .................. 546/256; 514/333
See application file for complete search history.

(56) References Cited

U.S. PATENT DOCUMENTS

| | | | |
|---|---|---|---|
| 3,226,394 A | 12/1965 | Schippet et al. | |
| 4,568,687 A | 2/1986 | Wright et al. | |
| 5,716,993 A | 2/1998 | Ozaki et al. | |
| 6,448,277 B2 | 9/2002 | Altmann et al. | |
| 6,548,548 B2 | 4/2003 | Campbell et al. | |
| 6,818,661 B2 | 11/2004 | Seidelmann et al. | |
| 6,878,720 B2 | 4/2005 | Altmann et al. | |
| 7,002,022 B2 | 2/2006 | Altmann et al. | |
| 7,122,547 B1 | 10/2006 | Huth et al. | |
| 7,148,357 B2 * | 12/2006 | Huth et al. | 546/275.7 |
| 7,202,260 B2 | 4/2007 | Huth et al. | |
| 7,307,088 B2 | 12/2007 | Huang et al. | |
| 7,429,592 B2 | 9/2008 | Ernst et al. | |
| 2002/0019414 A1 | 2/2002 | Altmann et al. | |
| 2002/0147198 A1 | 10/2002 | Chen et al. | |
| 2003/0134836 A1 | 7/2003 | Elbaum et al. | |
| 2003/0176469 A1 | 9/2003 | Seidelmann et al. | |
| 2003/0225106 A1 | 12/2003 | Askew et al. | |
| 2004/0029880 A1 | 2/2004 | Krueger et al. | |
| 2004/0039019 A1 | 2/2004 | Huth et al. | |
| 2004/0102441 A1 | 5/2004 | Krueger et al. | |
| 2004/0254185 A1 | 12/2004 | Ernst et al. | |
| 2004/0266770 A1 | 12/2004 | Ernst et al. | |
| 2005/0032816 A1 | 2/2005 | Ernst | |
| 2005/0054654 A1 | 3/2005 | Huth et al. | |
| 2005/0261343 A1 | 11/2005 | Krueger et al. | |
| 2006/0116380 A1 | 6/2006 | Bohlmann et al. | |
| 2006/0160861 A1 | 7/2006 | Bohlmann et al. | |
| 2006/0264425 A1 | 11/2006 | Bohlmann et al. | |
| 2007/0015794 A1 | 1/2007 | Huth et al. | |
| 2007/0135489 A1 | 6/2007 | Huth et al. | |

FOREIGN PATENT DOCUMENTS

| | | |
|---|---|---|
| DE | 2652144 A | 5/1978 |
| DE | 3406416 A1 | 8/1984 |
| DE | 19910396 A1 | 9/2000 |
| DE | 10023486 | 3/2002 |
| DE | 10228090 | 1/2004 |
| EP | 0564356 A1 | 10/1993 |
| EP | 0650961 A1 | 5/1995 |
| EP | 06/86625 A1 | 12/1995 |
| JP | 50157383 A | 12/1975 |
| WO | WO 9426260 A1 | 11/1994 |
| WO | WO 96/09294 A | 3/1996 |
| WO | WO 00/27819 | 5/2000 |
| WO | WO 00/27820 | 5/2000 |
| WO | WO 00/39118 A | 7/2000 |
| WO | WO 01/55114 A1 | 8/2001 |
| WO | WO 01/85715 A | 11/2001 |
| WO | WO 0185691 | 11/2001 |
| WO | WO 02055501 | 7/2002 |
| WO | WO 02/090352 A2 | 11/2002 |
| WO | WO 02066470 | 11/2002 |
| WO | WO 02090352 | 11/2002 |
| WO | WO 03/040102 | 5/2003 |
| WO | WO 03048158 | 6/2003 |
| WO | WO 2004/013102 | 2/2004 |

OTHER PUBLICATIONS

Augustin et al.: "Antiangiogenic Tumour Therapy: Will It Work?" Elsevier Trends Journal, vol. 19, No. 6, Jun. 1, 1998, pp. 216-222, XP004145666.
Strandtmann et al., J. Med. Chem. vol. 10, No. 6, 1967, pp. 1063-1065.
Sofina et al.: "Experimental Evaluation of Anti-Tumor Drugs in the USA and USSR and Clincal Correltaions," NCI Monograph 55, NIH Publication No. 80-1933 (1980).
Wermuth et al.: "The Practice of Medicinal Chemistry" Practice of Medicninal Chemistry XX, XX, 1996 pp. 203-237, XP002190259.
Montginoul et al.: "Analgesic, Anticonvulsant and Anti-Inflammatory Activities of 1H, 3H-Quinazoline-2,4-Diones" Chemical Abstracts Service, Coloumbus, Ohio, US; Retreived From STN Database Accession No. 110:165551H; XP002135868; Ann. Pharm. FR (1989) vol. 46, No. 4, pp. 223-232.
Noda et al.: "Quinazoline Compounds" Chemical Abstracts, Jul. 19, 1976, vol. 85, No. 3, XP002135867.
Hardtmann et al.: "Chemistry of 2H-3,1-Benzoxazine-2,4 (1H)-Dione (Isatoic Anhydrides). I. Sythesis of N-Substituted2H-3,1-Benzoxazine-2,4(1H)-Dione" Journal of Heterocyclic Chemistry, 1975,vol. 12, No. 3, pp. 565-572, Heterocorporation, XP002135866.
Pastor et al.: "Synthesis of New 1H,3H-Quinazoline-2,4-Diones", Bulletin de la Societe Chimique de France, vol. 5-6, No. 2, 1975, pp. 1331-1338, XP002135865.

(Continued)

Primary Examiner — Patricia L Morris
(74) Attorney, Agent, or Firm — Millen, White, Zelano & Branigan, P.C.

(57) ABSTRACT

The invention relates to novel nicotinamide pyridinureas as VEGF receptor kinase inhibitors, their production and use as pharmaceutical agents for preventing or treating diseases that are triggered by persistent angiogenesis.

22 Claims, No Drawings

OTHER PUBLICATIONS

Manley et al.: "Anthranilic Acid Amides: A Novel Class of Antiangiogenic VEGF Receptor Kinase Inhibitors", J. Med. Chem., 2002, vol. 45, pp. 5687-5693.
Golub et al. "Science" 1999, vol. 286, pp. 521-537.
Lala et al.: "Cancer and Metastasis Reviews" 1998, vol. 17, No. 1, pp. 91-106.
Verweij et al.: "Multi-Tatget Tyrosine Kinase Inhibition: and the Winner is . . . ", Journal of Clinical Oncology, vol. 25, No. 17, Jun. 10, 2007.
Hanrahan et al.: "Vascular Endothelial Growth Factor Receptor Tyrosine Kinase Inhibitors Vandetanib (ZD6474) and AZD217 in Lung Cancer", Cliical Cancer Search 2007; vol. 13 (15 Suppl) Aug. 1, 2007.
U.S. Appl. No. 10/631,018.
U.S. Appl. No. 11/525,091.
English Abstracts of Hardtmann et al.: "Chemistry of 2H-3,1-Benzoxazine-2,4 (1H)-Dione (Isatoic Anhydrides). I. Sythesis of N-Substituted2H-3,1-Benzoxazine-2,4(1H)-Dione" Journal of Heterocyclic Chemistry, 1975,vol. 12, No. 3, pp. 565-572, Heterocorporation, XP002135866.
English Abstracts of Pastor et al.: "Synthesis of New 1H,3H-Quinazoline-2,4-Diones", Bulletin de la Societe Chimique de France, vol. 5-6, No. 2, 1975, pp. 1331-1338, XP002135865.
Non Final Rejection Dated Dec. 5, 2008—U.S. Appl. No. 11/262,953, filed Nov. 1, 2005 (Publication No. 2006/0160861 A1).
Final Rejection Dated Dec. 17, 2008—U.S. Appl. No. 11/525,091, filed Sep. 22, 2006 (Publication No. 2007/0015794 A1).
Non Final Rejection Dated Mar. 17, 2008—U.S. Appl. No. 11/525,091, filed Sep. 22, 2006 (Publication No. 2007/0015794 A1).
Non Final Rejection Dated Oct. 8, 2008—U.S. Appl. No. 11/265,516, filed Nov. 3, 2005 (Publication No. 2006/0264426 A1).
Non Final Rejection Dated Dec. 6, 2005—U.S. Appl. No. 10/631,018, filed Jul. 31, 2003 (Publication No. 2004/0147535 A1).
Non Final Rejection Dated Nov. 24, 2004—U.S. Appl. No. 10/275,479, filed Jun. 23, 2003 (Publication No. 2004/00298880 A1).
Final Rejection Dated May 3, 2005—U.S. Appl. No. 10/275,480, filed Jun. 24, 2003 (Publication No. 2004/0102441 A1).
Non Final Rejection Dated Nov. 19, 2004—U.S. Appl. No. 10/275,480, filed Jun. 24, 2003 (Publication No. 2004/0102441 A1).
Non Final Rejection Dated Mar. 3, 2004—U.S. Appl. No. 10/275,480, filed Jun. 24, 2003 (Publication No. 2004/0102441 A1).
Non Final Rejection Dated Apr. 2, 2007—U.S. Appl. No. 10/476,761, filed Aug. 25, 2004 (Publication No. 2004/0266770 A1).
Non Final Rejection Dated Feb. 21, 2002—U.S. Appl. No. 09/831,506, filed Sep. 14, 2001.
Non Final Rejection Dated Jun. 12, 2002—U.S. Appl. No. 09/831,506, filed Sep. 14, 2001.
Final Rejection Dated Dec. 30, 2002—U.S. Appl. No. 09/831,506, filed Sep. 14, 2001.
Non Final Rejection Dated Mar. 25, 2004—U.S. Appl. No. 09/831,506, filed Sep. 14, 2001.
Final Rejection Dated Dec. 9, 2008—U.S. Appl. No. 10/477,119, filed Jun. 23, 2004 (Publication No. 2004/0254185 A1).
Non Final Rejection Dated Mar. 11, 2008—U.S. Appl. No. 10/477,119, filed Jun. 23, 2004 (Publication No. 2004/0254185 A1).
Non Final Rejction Dated Nov. 14, 2008—U.S. Appl. No. 11/265,517, filed Nov. 3, 2005 (Publication No. 2006/0116380 A1).
Carmeliet et al.: "Angiogenesis in Cancer and Other Diseases"; Macmilliam Magazines Ltd., 2000, vol. 407, p. 249-257.
English Abstract of JP 50157383 A.
English Abstract of DE 2652144 A.
English Abstract of EP 0564356 A1: 4-Phenylaminomethylimidazole Derivatives, Process for Their Preparation, Angiotensin II Receptor Antagonist and Their Application in Therapy [German] [French], Dodey, Pierre et al. Jan. 4, 1992.

* cited by examiner

NICOTINAMIDE PYRIDINUREAS AS VASCULAR ENDOTHELIAL GROWTH FACTOR (VEGF) RECEPTOR KINASE INHIBITORS

This application claims the benefit of the filing date of U.S. Provisional Application Ser. No. 60/626,914 filed Nov. 12, 2004.

The invention relates to novel anthranilamide pyridinureas as VEGF receptor kinase inhibitors, their production and use as pharmaceutical agents for preventing or treating diseases that are triggered by persistent angiogenesis.

Many diseases are known to be associated with persistent angiogenesis, for example, diseases such as tumor- or metastases-growth; psoriasis; arthritis, such as rheumatoid arthritis, hemangioma, endometriosis, angiofibroma; eye diseases, such as diabetic retinopathy, neovascular glaucoma; renal diseases, such as glomerulonephritis, diabetic nephropathy, malignant nephrosclerosis, thrombotic microangiopathic syndrome, transplant rejections and glomerulopathy; fibrotic diseases, such as cirrhosis of the liver, mesangial cell proliferative diseases and arteriosclerosis.

Lymphangiogenesis is a process accompanying tumor growth and metastases. It is prominent in lymphedema, lymphangiectasia, lymphangioma, and lymphangiosarcoma and in asthmatic disease, where lymph vessels are chronically overexpressed in the lung.

Persistent angiogenesis is induced by the factor VEGF via its receptors. In order for VEGF to exert this action, it is necessary that VEGF bind to the receptor, and that a tyrosine phosphorylation is induced.

Direct or indirect inhibition of the VEGF receptor can be used for preventing or treating such diseases and other VEGF-induced pathological angiogenesis and vascular permeable conditions, such as tumor vascularization. For example, it is known that the growth of tumors can be inhibited by soluble receptors and antibodies against VEGF, an example for the latter being Avastin® whose treatment paradigm has been introduced in human cancer therapy.

Anthranilic acid amides effective in the treatment of psoriasis; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases, arteriosclerosis, injuries to nerve tissue, and for inhibiting the reocclusion of vessels after balloon catheter treatment, in vascular prosthetics or after mechanical devices are used to keep vessels open, such as, e.g., stents, have been reported in WO 00/27820.

Anthranilic acid amides that are effective in the treatment of tumor or metastasis growth, psoriasis, Kaposi's sarcoma, restenosis, such as, e.g., stent-induced restenosis, endometriosis, Crohn's disease, Hodgkin's disease, leukemia; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases, arteriosclerosis, injuries to nerve tissue, and for inhibiting the reocclusion of vessels after balloon catheter treatment, in vascular prosthetics or after mechanical devices are used to keep vessels open, such as, e.g., stents, as immunosuppressive agents, as a support in scar-free healing, in senile keratosis and in contact dermatitis have also been reported in WO 04/13102.

There is, however, a desire to produce compounds that are as efficacious as possible in as broad a range of indications as possible. A constant blockade of VEGF mediated signal transduction is desirable in order to reduce persistent angiogenesis and lymphangiogenesis. Suitable compounds for longer term treatment should exhibit little or no drug-drug interaction potential. The Cytochrome P450 isoenzymes play a pivotal role in the degradation of pharmaceutical agents. The problem is also complicated by the fact that patients may express different relative amounts of the isoenzymes. An inhibition of these isoenzymes may result in undesirable pharmaceutical agent interactions, especially in the case of multimorbid patients (patients with multiple disease conditions). For example, inhibition of the Cytochrome P450 isoenzymes responsible for metabolisation of the parent agent could lead to toxic systemic concentrations. A further problem exists in combination therapy with other medications, whereby inhibition of the Cytochrome P450 isoenzymes responsible for metabolising the co-medications could lead to toxic systemic concentrations of the co-medication. This is especially the case for co-administered cytostatics in the case of cancer therapy.

Thus, it has now surprisingly been found that compounds of general formula (I), as described below, have more advantageous physico-chemical and/or pharmacokinetic properties and prevent, for example, tyrosine phosphorylation or stop persistent angiogenesis and thus the growth and propagation of tumors, whereby they are distinguished in particular by a potent inhibition of VEGF receptor kinases and a reduced potential for drug-drug interactions, specifically a reduced inhibition of cytochrome P450 isoenzymes 2C9 and 2C19.

The compounds of formula (I) are thus suitable, for example, for the treatment or prevention of diseases for which an inhibition of angiogenesis and/or the VEGF receptor kinases is beneficial.

In one aspect of the invention, there is provide a nicotinamide pyridinurea compound of formula (I):

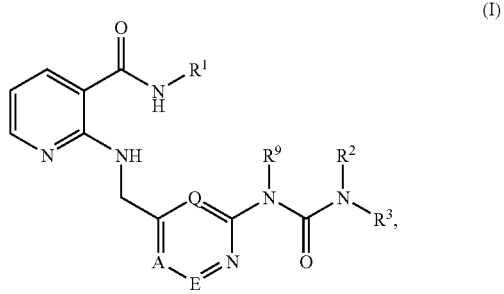

wherein:
A, E and Q independently of one another, are CH or N, whereby only a maximum of two nitrogen atoms are contained in the ring; preferably A, E, and Q are each CH;

$R^1$ is aryl or heteroaryl, which may be optionally substituted in one or more places in the same way or differently with halogen, hydroxy, $C_1$-$C_{12}$-alkyl, $C_3$-$C_6$-cycloalkyl, $C_2$-$C_6$-alkenyl, $C_2$-$C_6$-alkynyl, aralkyloxy, $C_1$-$C_{12}$-alkoxy, halo-$C_1$-$C_6$-alkyl, cyano-$C_1$-$C_6$-alkyl, =O, —$SO_2R^6$, —$OR^5$, —$SOR^4$, —$COR^6$, —$CO_2R^6$ or —$NR^7R^8$, whereby $C_1$-$C_{12}$-alkyl may be substituted with —$OR^5$ or —$NR^7R^8$; preferably phenyl, isoquinolyl, quinolinyl or indazolyl optionally substituted in one or more places in the same way or differently with halogen, hydroxy, $C_1$-$C_{12}$-alkyl, $C_3$-$C_6$-cycloalkyl, $C_2$-$C_6$-alkenyl, $C_2$-$C_6$-alkynyl, aralkyloxy, $C_1$-$C_{12}$-alkoxy, halo-$C_1$-$C_6$-alkyl, cyano-$C_1$-$C_6$-alkyl, =O, —SO$_2$R$^6$, —OR$^5$, —SOR$^4$, —COR$^6$, —CO$_2$R$^6$ or —NR$^7$R$^8$, whereby $C_1$-$C_{12}$-alkyl may be substituted with —OR$^5$ or —NR$^7$R$^8$; more preferably indazolyl substituted in one or more places in the same way or differently with halogen, hydroxy, $C_1$-$C_{12}$-alkyl, $C_3$-$C_6$-cycloalkyl, $C_2$-$C_6$-alkenyl, $C_2$-$C_6$-alkynyl, aralkyloxy, $C_1$-$C_{12}$-alkoxy, halo-$C_1$-$C_6$-alkyl, cyano-$C_1$-$C_6$-alkyl, =O, —SO$_2$R$^6$, —OR$^5$, —SOR$^4$, —COR$^6$, —CO$_2$R$^6$ or —NR$^7$R$^8$, whereby $C_1$-$C_{12}$-alkyl may be substituted with —OR$^5$ or —NR$^7$R$^8$; even more preferably indazolyl substituted with $C_1$-$C_{12}$-alkyl; more preferably indazolyl substituted with —CH$_3$, particularly 2-methyl-indazolyl;

R$^2$, R$^3$ and R$^9$ independently of one another, are hydrogen or $C_1$-$C_{12}$ alkyl optionally substituted with halogen, —OR$^5$, or $C_1$-$C_{12}$-alkoxy; preferably hydrogen or unsubstituted $C_1$-$C_{12}$ alkyl; more preferably hydrogen or —CH$_3$; or R$^9$ is hydrogen, and R$^2$ and R$^3$ together with the nitrogen atom to which they are attached form a 3-8 membered heterocycloalkyl ring, preferably a 4-7 membered heterocycloalkyl ring, which may optionally contain further heteroatoms, such as nitrogen, oxygen or sulphur, and which may be optionally substituted in one or more places in the same way or differently with halogen, cyano, $C_1$-$C_{12}$-alkyl, $C_1$-$C_{12}$-alkoxy, halo-$C_1$-$C_6$-alkyl, =O, —OR$^5$, —SR$^4$, —SOR$^4$, —SO$_2$R$^6$, —COR$^6$, or —CO$_2$R$^6$, whereby $C_1$-$C_{12}$ alkyl optionally can also be substituted with a group —OR$^5$; preferably R$^2$ and R$^3$ together with the nitrogen atom to which they are attached form a 5 or 6 membered heterocycloalkyl ring, which contains no or at least one further heteroatom, such as nitrogen, oxygen or sulphur, and which may be optionally substituted in one or more places in the same way or differently with halogen, cyano, $C_1$-$C_{12}$-alkyl, $C_1$-$C_{12}$-alkoxy, halo-$C_1$-$C_6$-alkyl, =O, —OR$^5$, —SR$^4$, —SOR$^4$, —SO$_2$R$^6$, —COR$^6$, or —CO$_2$R$^6$, whereby $C_1$-$C_{12}$ alkyl optionally can also be substituted with a group —OR$^5$; or R$^3$ is hydrogen or $C_1$-$C_{12}$-alkyl, whereby $C_1$-$C_{12}$ alkyl optionally can also be substituted with a group —OR$^5$; preferably is hydrogen or —CH$_3$; more particularly preferred hydrogen, and R$^2$ and R$^9$ together with the two nitrogen atoms to which they are attached form a 5-7 membered ring, preferably a 5 or 6 membered ring, which may be optionally further substituted in one or more places in the same way or differently with halogen, $C_1$-$C_{12}$-alkyl, $C_1$-$C_{12}$-alkoxy, halo-$C_1$-$C_6$-alkyl, or =O, whereby $C_1$-$C_{12}$ alkyl optionally can also be substituted with a group —OR$^5$; preferably together with the two nitrogen atoms to which they are attached form a 5-7 membered saturated ring, preferably a 5 or 6 membered saturated ring, which may be optionally further substituted in one or more places in the same way or differently with halogen, $C_1$-$C_{12}$-alkyl, $C_1$-$C_{12}$-alkoxy, halo-$C_1$-$C_6$-alkyl, or =O, whereby $C_1$-$C_{12}$ alkyl optionally can also be substituted with a group —OR$^5$; more preferably together with the two nitrogen atoms to which they are attached form a 5 membered saturated ring, optionally further substituted in one or more places in the same way or differently with halogen, $C_1$-$C_{12}$-alkyl, $C_1$-$C_{12}$-alkoxy, halo-$C_1$-$C_6$-alkyl, or =O, whereby $C_1$-$C_{12}$ alkyl optionally can also be substituted with a group —OR$^5$;

R$^4$ is $C_1$-$C_{12}$-alkyl, $C_3$-$C_8$-cycloalkyl, aryl or heteroaryl; preferably $C_1$-$C_{12}$-alkyl; more preferably —CH$_3$;

R$^5$ is hydrogen, $C_1$-$C_{12}$-alkyl, $C_3$-$C_8$-cycloalkyl or halo-$C_1$-$C_6$-alkyl; preferably —CH$_3$ or hydrogen; more preferably hydrogen;

R$^6$ is hydrogen, $C_1$-$C_{12}$-alkyl, $C_3$-$C_8$-cycloalkyl, halo-$C_1$-$C_6$-alkyl, aryl, or —NR$^7$R$^8$; preferably $C_1$-$C_{12}$-alkyl or —NR$^7$R$^8$; more preferably —CH$_3$;

R$^7$ and R$^8$ independently of one another, are hydrogen, —SO$_2$R$^6$, —COR$^6$, aryl, $C_3$-$C_8$-cycloalkyl, $C_1$-$C_{12}$-alkyl, halo-$C_1$-$C_{12}$-alkyl, or $C_1$-$C_{12}$-alkoxy, whereby $C_1$-$C_{12}$-alkyl may be optionally substituted with —OR$^5$ or —N(CH$_3$)$_2$, or R$^7$ and R$^8$ may also be chosen in such a way as to provide a 3-8 membered cycloalkyl ring, preferably a 4-7 membered cycloalkyl ring, more preferably a 5 or 6 membered ring, which may optionally contain further heteroatoms, such as nitrogen, oxygen or sulphur, and may be optionally substituted in one or more places in the same way or differently with halogen, cyano, $C_1$-$C_{12}$-alkyl, $C_1$-$C_{12}$-alkoxy, halo-$C_1$-$C_6$-alkyl, =O, —OR$^5$, COR$^6$, —SR$^4$, —SOR$^4$ or —SO$_2$R$^6$; preferably R$^7$ and R$^8$ independently of one another, are hydrogen, COR$^6$, —SO$_2$R$^6$, $C_1$-$C_{12}$-alkyl; more preferably hydrogen or $C_1$-$C_{12}$-alkyl; more preferably hydrogen or —CH$_3$, and as well as isomers, diastereoisomers, enantiomers, tautomers and salts thereof.

In a second aspect of the present invention, there is provided a pharmaceutical agent comprising at least one compound of formula (I) or an isomer, diastereoisomer, enantiomer, tautomer or salt thereof.

In a third aspect of the present invention, there is provided a pharmaceutical agent comprising at least one compound of formula (I) or an isomer, diastereoisomer, enantiomer, tautomer or salt thereof and at least one pharmaceutically acceptable carrier, diluent or excipient.

In a fourth aspect of the present invention, there is provided a pharmaceutical agent comprising at least one compound of formula (I) or an isomer, diastereoisomer, enantiomer, tautomer or salt thereof for use in the prevention or treatment of diseases associated with persistent angiogenesis and/or diseases associated with excessive lymphangiogenesis.

In a fifth aspect of the present invention, there is provided a pharmaceutical agent comprising at least one compound of formula (I) or an isomer, diastereoisomer, enantiomer, tautomer or salt thereof for use in the prevention or treatment of tumor- or metastases-growth; psoriasis; Karposi's sarcoma; restenosis including stent-induced restenosis; Crohn's disease; Hodgkin's disease; leukemia; arthritis including rheumatoid arthritis, hemangioma, angiofibroma; endometriosis; eye diseases including diabetic retinopathy, neovascular glaucoma; corneal transplants; renal diseases, including glomerulonephritis, diabetic nephropathy, malignant nephrosclerosis, thrombotic microangiopathic syndrome, transplant rejections and glomerulopathy; fibrotic diseases, including cirrhosis of the liver; mesangial cell proliferative diseases; arteriosclerosis; injuries to the nerve tissue, and for inhibiting the reocclusion of vessels after balloon catheter treatment; in vascular prosthetics or after mechanical devices are used to keep vessels open, as immunosuppresive agent for supporting scar-free healing; senile keratosis; contact dermatitis; and asthma.

In a sixth aspect of the present invention, there is provided a pharmaceutical agent comprising at least one compound of formula (I) or an isomer, diastereoisomer, enantiomer, tautomer or salt thereof for use as VEGF receptor kinase 3-inhibitors of lymphangiogenesis.

In a seventh aspect of the present invention, there is provided a pharmaceutical agent comprising at least one compound of formula (I) or an isomer, diastereoisomer, enantiomer, tautomer or salt thereof for use in a method for the treatment of the human or animal body.

In a eighth aspect of the present invention, there is provided a pharmaceutical agent comprising at least one compound of formula (I) or an isomer, diastereoisomer, enantiomer, tautomer or salt thereof for use in the preparation of a pharmaceutical product for the treatment of a disease for which an inhibition of angiogenesis and/or lymphangiogenesis and/or the VEGF receptor kinases is beneficial.

In a ninth aspect of the present invention, there is provided a pharmaceutical agent comprising at least one compound of formula (I) or an isomer, diastereoisomer, enantiomer, tautomer or salt thereof for use as an inhibitor of the tyrosine kinases VEGFR-1 and VEGFR-2.

In a tenth aspect of the present invention, there is provided a compound of general formula (III):

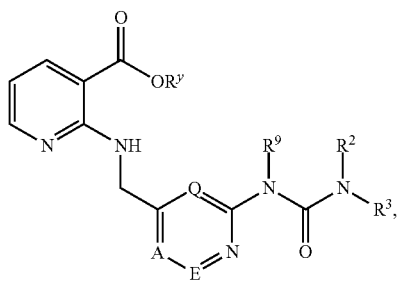

(III)

in which A, E, Q, $R^2$, $R^3$ and $R^9$, are as defined for formula (I) supra and $R^y$ is H or $C_1$-$C_6$-alkyl, as an intermediate for the preparation of a compound of formula (I) as defined supra. Preferably $R^y$ is H or $C_1$-$C_2$-alkyl; more preferably $R^y$ is H or —$CH_3$.

In an eleventh aspect of the present invention, there is provided a compound of general formula (IIIA):

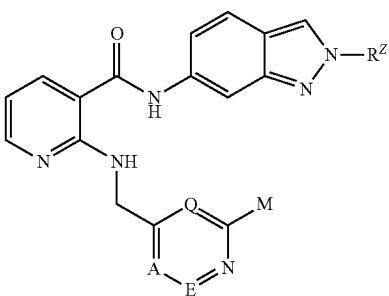

(IIIA)

in which A, E, Q, W and are as defined for formula (I) supra, $R^Z$ is $C_1$-$C_{12}$-alkyl and M is halogen, as an intermediate for the preparation of a compound of formula (I) as defined supra. Preferably, M=a chlorine atom.

In a twelfth aspect of the present invention, there is provided the use of a compound of general formula (III), in which A, E, Q, $R^2$, $R^3$ and $R^9$ are as defined for formula (I) supra and $R^y$ is H or $C_1$-$C_6$-alkyl, or of a compound of general formula (IIIA), in which A, E, Q, M, and $R^1$ are as defined for formula (I) supra, as an intermediate for the preparation of a compound of formula (I), supra.

In a thirteenth aspect of the present invention, there is provided a process for the preparation of a compound of formula (I), wherein all substituents are as described in claim 1, in which a compound of formula (III), wherein A, E, Q, $R^2$, $R^3$ and $R^9$ are as defined in claim 1 and $R^y$ is H or $C_1$-$C_6$-alkyl, is reacted with an amine of formula $R^1NH_2$ in which $R^1$ is as defined in claim 1.

In a fourteenth aspect of the present invention, there is provided a process for the preparation of a compound of formula (I), wherein all substituents are as described in claim 1, in which a compound of formula (II):

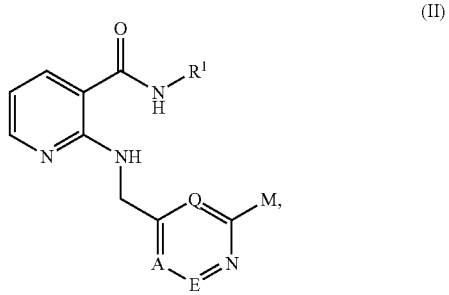

(II)

wherein A, E, Q, and $R^1$ are as defined in claim 1 and M stands for halogen, is:
(i) first converted to an amine and subsequently converted to a compound of formula (I) by reaction with a carbamoyl chloride of formula $ClCONR^2R^3$, wherein $R^2$ and $R^3$ are as defined in claim 1; or, alternatively,
(ii) reacted with a compound of formula $R^9HNCONR^2R^3$, wherein $R^2$, $R^3$ and $R^9$ are as defined in claim 1, or, alternatively,
(iii) first converted to an amine and subsequently converted to a compound of formula (I) by first reacting with a compound of formula $ClCO_2Ph$ and then reacting with a compound of formula $HNR^2R^3$, wherein $R^2$ and $R^3$ are as defined in claim 1. Preferably a compound of formula (I) is prepared using the (ii) process.

As used herein, the term "alkyl" is defined in each case as a substituted or unsubstituted straight-chain or branched alkyl group, such as, for example, methyl, ethyl, propyl, isopropyl, butyl, isobutyl, tert-butyl, pentyl, isopentyl or hexyl, heptyl, octyl, nonyl, decyl, undecyl, or dodecyl.

As used herein, the term "alkoxy" is defined in each case as a straight-chain or branched alkoxy group, such as, for example, methyloxy, ethyloxy, propyloxy, isopropyloxy, butyloxy, isobutyloxy, tert-butyloxy, pentyloxy, isopentyloxy, hexyloxy, heptyloxy, octyloxy, nonyloxy, decyloxy, undecyloxy or dodecyloxy.

As used herein, the term "cycloalkyl" is defined as a monocyclic alkyl ring, such as cyclopropyl, cyclobutyl, cyclopentyl, cyclohexyl, or cycloheptyl, cyclooctyl, cyclononyl or cyclodecyl, and also as bicyclic rings or tricyclic rings, such as, for example, adamantanyl. The cycloalkyl group may also contain, one or more heteroatoms, such as oxygen, sulphur and/or nitrogen, such that a heterocycloalkyl ring is formed.

As used herein, the term "heterocycloalkyl", as used throughout this text, e.g. as used in the definition of "$R^2$ and $R^3$ together with the nitrogen atom to which they are attached form a 3-8 membered heterocycloalkyl ring" is defined as a nitrogen atom-containing monocyclic alkyl ring which optionally contains at least one further heteroatom, such as oxygen, sulphur and/or nitrogen, it being understood that said nitrogen atom links the heterocycloalkyl ring to the rest of the molecule. Preferred are 3-8 membered heterocycloalkyl rings, more preferably 4-7 membered heterocycloalkyl rings.

Even more preferred are 5 or 6 membered heterocycloalkyl rings. For example, a heterocycloalkyl ring such as one selected from the following list can be mentioned:

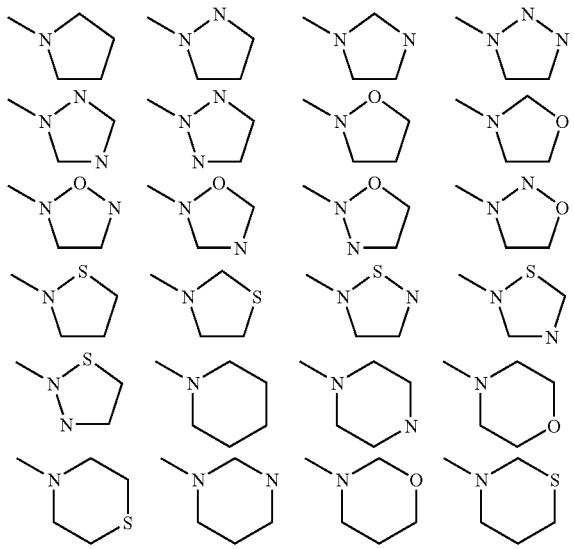

It is understood that any of the above structures may contain at least one additional heteroatom, such as nitrogen, oxygen or sulphur.

In particular, the following heterocycloalkyl rings can be mentioned: tetrahydrofuran, tetrahydropyran, pyrrolidine, piperidine, morpholine, piperazine and thiomorpholine. The heterocycloalkyl ring may be optionally substituted in one or more places in the same way or differently with, for example, halogen, cyano, $C_1$-$C_{12}$-alkyl, $C_1$-$C_{12}$-alkoxy, halo-$C_1$-$C_6$-alkyl, =O, —OR$^5$, —SR$^4$, —SOR$^4$ or —SO$_2$R$^6$, —COR$^6$, —CO$_2$R$^6$, whereby $C_1$-$C_{12}$ alkyl optionally can also be substituted with a group —OR$^5$. It is understood that the substitution on any of the above-mentioned heterocycloalkyl rings may take place on any one of the heterocycloalkyl ring's carbon atoms and/or on any one of the heterocycloalkyl ring's heteroatoms. Preferably the heterocycloalkyl ring is substituted in one or two places.

As used herein, the term "halogen" is defined in each case as fluorine, chlorine, bromine or iodine, with fluorine being preferred for compounds of formula (I) and chlorine and bromine being preferred as substituent M in compounds of formula (II), (III), or (IIIA).

As used herein, the term "halo-$C_1$-$C_6$-alkyl" is defined as a $C_1$-$C_6$ alkyl group wherein some or all hydrogen atoms are replaced by halogen atoms, preferably replaced by one or more fluoro atoms. Preferred is the group CF$_3$.

As used herein, the term "alkenyl" is defined in each case as a straight-chain or branched alkenyl group that contains 2-6, preferably 2-4 carbon atoms. For example, the following groups can be mentioned: vinyl, propen-1-yl, propen-2-yl, but-1-en-1-yl, but-1-en-2-yl, but-2-en-1-yl, but-2-en-2-yl, 2-methyl-prop-2-en-1-yl, 2-methyl-prop-1-en-1-yl, but-1-en-3-yl, but-3-en-1-yl, and allyl.

As used herein, the term "aryl" is defined in each case as having 3-12 carbon atoms, preferably 6-12 carbon atoms, such as, for example, cyclopropenyl, cyclopentadienyl, phenyl, tropyl, cyclooctadienyl, indenyl, naphthyl, azulenyl, biphenyl, fluorenyl, anthracenyl etc, phenyl being preferred.

As used herein, the term "$C_1$-$C_{12}$", as used throughout this text e.g. in the context of the definitions of "$C_1$-$C_{12}$-alkyl" and "$C_1$-$C_{12}$-alkoxy", is to be understood as meaning an alkyl or alkoxy group having a finite number of carbon atoms of 1 to 12, i.e. 1, 2, 3, 4, 5, 6, 7, 8, 9, 10, 11 or 12 carbon atoms. It is to be understood further that said term "$C_1$-$C_{12}$" is to be interpreted as any subrange comprised therein, e.g. $C_1$-$C_{12}$, $C_2$-$C_{11}$, $C_3$-$C_{10}$, $C_4$-$C_9$, $C_5$-$C_8$, $C_6$-$C_7$, $C_1$-$C_2$, $C_1$-$C_3$, $C_1$-$C_4$, $C_1$-$C_5$, $C_1$-$C_6$, $C_1$-$C_7$, $C_1$-$C_8$, $C_1$-$C_9$, $C_1$-$C_{10}$, $C_1$-$C_{11}$; preferably $C_1$-$C_2$, $C_1$-$C_3$, $C_1$-$C_4$, $C_1$-$C_5$, $C_1$-$C_6$; more preferably $C_1$-$C_3$.

Similarly, as used herein, the term "$C_2$-$C_6$", as used throughout this text e.g. in the context of the definitions of "$C_2$-$C_6$-alkenyl", is to be understood as meaning an alkenyl group having a finite number of carbon atoms of 2 to 6, i.e. 2, 3, 4, 5, or 6 carbon atoms. It is to be understood further that said term "$C_2$-$C_6$" is to be interpreted as any subrange comprised therein, e.g. $C_2$-$C_6$, $C_3$-$C_5$, $C_3$-$C_4$, $C_2$-$C_3$, $C_2$-$C_4$, $C_2$-$C_5$; preferably $C_2$-$C_3$.

Further as used herein, the term "$C_1$-$C_6$", as used throughout this text e.g. in the context of the definitions of "halo-$C_1$-$C_6$-alkyl", is to be understood as meaning a haloalkyl group having a finite number of carbon atoms of 1 to 6, i.e. 1, 2, 3, 4, 5, or 6 carbon atoms. It is to be understood further that said term "$C_1$-$C_6$" is to be interpreted as any subrange comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$, $C_1$-$C_6$; more preferably $C_1$-$C_3$.

As used herein, the term "heteroaryl" as defined in each case, is an aromatic ring system which contains, in the ring, at least one heteroatom which contains at least one heteroatom which may be identical or different, and which comprises 3-16 ring atoms, preferably 5 or 6 or 9 or 10 atoms, said heteroatom being such as oxygen, nitrogen or sulphur, and can be monocyclic, bicyclic, or tricyclic, and in addition in each case can be benzocondensed. Preferably, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, etc., and benzo derivatives thereof, such as, e.g., benzofuranyl, benzothienyl, benzoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, e.g., quinolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl, etc. More preferably the heteroaryl is selected from quinolinyl, isoquinolinyl, or indazolyl. More preferably still, the heteroaryl is indazolyl.

The aryl group and the heteroaryl group in each case can be substituted in the same way or differently in one or more places with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —SO$_2$R$^6$, —OR$^5$, —SOR$^4$, —COR$^6$, —CO$_2$R$^6$ or —NR$^7$R$^8$, whereby $C_1$-$C_{12}$-alkyl may be substituted with —NR$^7$R$^8$. It is understood that the substitution on the aryl group and the heteroaryl group may take place on any one of the group's carbon atoms and/or on any one of the heteroatoms. Preferably the aryl group and the heteroaryl group is substituted in one or two places.

If an acid group is included, the physiologically compatible salts of organic and inorganic bases are suitable as salts, such as, for example, the readily soluble alkali salts and alkaline-earth salts as well as N-methyl-glucamine, dimethyl-glucamine, ethyl-glucamine, lysine, 1,6-hexadiamine, ethanolamine, glucosamine, sarcosine, serinol, tris-hydroxy-methyl-amino-methane, aminopropanediol, Sovak base, and 1-amino-2,3,4-butanetriol.

If a basic group is included, the physiologically compatible salts of organic and inorganic acids are suitable, such as hydrochloric acid, sulphuric acid, phosphoric acid, citric acid, tartaric acid, succinic acid, fumaric acid.

The compounds of general formula (I) according to the invention also contain the possible tautomeric forms and comprise the E-isomers or Z-isomers, or, if one or more stereogenic centers are present, racemates and/or enantiomers and/or diastereoisomers. Thus, a molecule with a single stereogenic center may be a mixture of enantiomers (R,S), or may be a single (R) or (S) enantiomer. A molecule with more than one stereogenic center may be a mixture of diastereoisomers, or may be a single diastereoisomer, whereby the diastereoisomers may also exist as mixtures of enantiomers or single enantiomers.

One embodiment of the present invention are compounds of formula (I) wherein A, E, and Q are each CH.

In one embodiment, $R^1$ is aryl or heteroaryl, which may be optionally substituted in one or more places in the same way or differently with halogen, hydroxy, $C_1$-$C_{12}$-alkyl, $C_3$-$C_6$-cycloalkyl, $C_2$-$C_6$-alkenyl, $C_2$-$C_6$-alkynyl, aralkyloxy, $C_1$-$C_{12}$-alkoxy, halo-$C_1$-$C_6$-alkyl, cyano-$C_1$-$C_6$-alkyl, =O, —$SO_2R^6$, —$OR^5$, —$SOR^4$, —$COR^6$, —$CO_2R^6$ or —$NR^7R^8$, whereby $C_1$-$C_{12}$-alkyl may be substituted with —OR or —$NR^7R^8$. In another embodiment, $R^1$ is phenyl, isoquinolinyl, quinolinyl or indazolyl optionally substituted in one or more places in the same way or differently with halogen, hydroxy, $C_1$-$C_{12}$-alkyl, $C_3$-$C_6$-cycloalkyl, $C_2$-$C_6$-alkenyl, $C_2$-$C_6$-alkynyl, aralkyloxy, $C_1$-$C_{12}$-alkoxy, halo-$C_1$-$C_6$-alkyl, cyano-$C_1$-$C_6$-alkyl, =O, —$SO_2R^6$, —$OR^5$, —$SOR^4$, —$COR^6$, —$CO_2R^6$ or —$NR^7R^8$, whereby $C_1$-$C_{12}$-alkyl may be substituted with —$OR^5$ or —$NR^7R^8$. In a preferred embodiment, $R^1$ is indazolyl substituted in one or more places in the same way or differently with halogen, hydroxy, $C_1$-$C_{12}$-alkyl, $C_3$-$C_6$-cycloalkyl, $C_2$-$C_6$-alkenyl, $C_2$-$C_6$-alkynyl, aralkyloxy, $C_1$-$C_{12}$-alkoxy, halo-$C_1$-$C_6$-alkyl, cyano-$C_1$-$C_6$-alkyl, =O, —$SO_2R^6$, —$OR^5$, —$SOR^4$, —COR, —$CO_2R^6$ or —$NR^7R^8$, whereby $C_1$-$C_{12}$-alkyl may be substituted with —$OR^5$ or —$NR^7R^8$. In a more preferred embodiment, $R^1$ is indazolyl substituted with $C_1$-$C_{12}$-alkyl, optionally having a halogen atom substituent, preferably a fluorine, chlorine, bromine, or iodine atom. In an even more preferred embodiment, $R^1$ is indazolyl substituted with —$CH_3$. In an even more particularly preferred embodiment, $R^1$ is 2-methyl-indazolyl.

In one embodiment, $R^2$, $R^3$ and $R^9$ independently of one another, are hydrogen or $C_1$-$C_{12}$ alkyl optionally substituted with halogen, —$OR^5$, or $C_1$-$C_{12}$-alkoxy. In a preferred embodiment $R^2$, $R^3$ and $R^9$ independently of one another, are hydrogen or $C_1$-$C_{12}$ alkyl. In a more preferred embodiment $R^2$ and $R^3$ independently of one another are hydrogen or —$CH_3$ and $R^9$ is hydrogen.

In another embodiment, $R^9$ is hydrogen and $R^2$ and $R^3$ together with the nitrogen atom to which they are attached form a 3-8 membered heterocycloalkyl ring, preferably a 4-7 membered heterocycloalkyl ring, which may optionally contain further heteroatoms, such as nitrogen, oxygen or sulphur, and which may be optionally substituted in one or more places in the same way or differently with halogen, cyano, $C_1$-$C_{12}$-alkyl, $C_1$-$C_{12}$-alkoxy, halo-$C_1$-$C_6$-alkyl, =O, —$OR^5$, —$SR^4$, —$SOR^4$, —$SO_2R^6$, —$COR^6$, or —$CO_2R^6$, whereby $C_1$-$C_{12}$ alkyl optionally can also be substituted with a group —$OR^5$. In a preferred embodiment, $R^9$ is hydrogen and $R^2$ and $R^3$ together with the nitrogen atom to which they are attached form a 5 or 6 membered heterocycloalkyl ring, which contains no or at least one further heteroatom, such as nitrogen, oxygen or sulphur, and which may be optionally substituted in one or more places in the same way or differently with halogen, cyano, $C_1$-$C_{12}$-alkyl, $C_1$-$C_{12}$-alkoxy, halo-$C_1$-$C_6$-alkyl, =O, —$OR^5$, —$SR^4$, —$SOR^4$, —$SO_2R^6$, —$COR^6$, or —$CO_2R^6$, whereby $C_1$-$C_{12}$ alkyl optionally can also be substituted with a group —$OR^5$.

In another embodiment, $R^3$ is hydrogen or $C_1$-$C_{12}$-alkyl, whereby $C_1$-$C_{12}$ alkyl optionally can also be substituted with a group —$OR^5$ and $R^2$ and $R^9$ together with the two nitrogen atoms to which they are attached form a 5-7 membered ring, preferably a 5 or 6 membered ring, which may be optionally further substituted in one or more places in the same way or differently with halogen, $C_1$-$C_{12}$-alkyl, $C_1$-$C_{12}$-alkoxy, halo-$C_1$-$C_6$-alkyl, or =O, whereby $C_1$-$C_{12}$ alkyl optionally can also be substituted with a group —$OR^5$. In a preferred embodiment, $R^3$ is hydrogen or —$CH_3$ and $R^2$ and $R^9$ together with the two nitrogen atoms to which they are attached form a 5-7 membered saturated ring, preferably a 5 or 6 membered saturated ring, which may be optionally further substituted in one or more places in the same way or differently with halogen, $C_1$-$C_{12}$-alkyl, $C_1$-$C_{12}$-alkoxy, halo-$C_1$-$C_6$-alkyl, or =O, whereby $C_1$-$C_{12}$ alkyl optionally can also be substituted with a group —$OR^5$. In a more preferred embodiment, $R^3$ is hydrogen and $R^2$ and $R^9$ together with the two nitrogen atoms to which they are attached form a 5 membered saturated ring optionally further substituted in one or more places in the same way or differently with halogen, $C_1$-$C_{12}$-alkyl, $C_1$-$C_{12}$-alkoxy, halo-$C_1$-$C_6$-alkyl, or =O, whereby $C_1$-$C_{12}$ alkyl optionally can also be substituted with a group —$OR^5$.

In one embodiment, $R^4$ is $C_1$-$C_{12}$-alkyl. In a preferred embodiment, $R^4$ is —$CH_3$.

In one embodiment, $R^5$ is —$CH_3$ or hydrogen. In a preferred embodiment, $R^5$ is hydrogen.

In one embodiment, $R^6$ is $C_1$-$C_{12}$-alkyl or —$NR^7R^8$. In a preferred embodiment, $R^6$ is $C_1$-$C_{12}$-alkyl. In a more preferred embodiment, $R^6$ is —$CH_3$.

In one embodiment, $R^7$ and $R^8$ independently of one another, are hydrogen, $COR^6$, $SO_2R^6$, $C_1$-$C_{12}$-alkyl. In a preferred embodiment, $R^7$ and $R^8$ independently of one another are hydrogen or —$CH_3$.

Some specific examples of compounds of the present invention include the following:

N-(2-methyl-2H-indazol-6-yl)-2-{[2-(3-methyl-ureido)-pyridin-4-ylmethyl]-amino}-nicotinamide, 2-{[2-(3-methyl-ureido)-pyridin-4-ylmethyl]-amino}-N-(3-trifluoromethyl-phenyl)-nicotinamide, N-(1-methyl-1H-indazol-6-yl)-2-{[2-(3-methyl-ureido)-pyridin-4-ylmethyl]-amino}-nicotinamide, N-isoquinolin-3-yl-2-{[2-(3-methyl-ureido)-pyridin-4-ylmethyl]-amino}-nicotinamide, N-(1-methyl-1H-indazol-5-yl)-2-{[2-(3-methyl-ureido)-pyridin-4-ylmethyl]-amino}-nicotinamide, morpholine-4-carboxylic acid (4-{[3-(2-methyl-2H-indazol-6-ylcarbamoylpyridin-2ylamino]-methyl}-pyridin-2-yl)-amide, 2-{[2-(3,3-dimethyl-ureido)-pyridin-4-ylmethyl]-amino}-N-(2-methyl-2H-indazol-6-yl)-nicotinamide, N-(2-methyl-2H-indazol-6-yl)-2-({2-[3-(1-methyl-piperidin-4-yl)-ureido]-pyridin-4-ylmethyl}-amino)-nicotinamide, and N-(2-methyl-2H-indazol-6-yl)-2-{[2-(2-oxo-imidazolidin-1-yl)-pyridin-4-ylmethyl]-aminoo}-nicotinamide;

as well as isomers, diastereoisomers, enantiomers, tautomers and salts thereof.

The compounds of formula (I) can be used as pharmaceutical agents based on their inhibitory activity relative to the phosphorylation of VEGF receptors. Based on their profile of action, the compounds according to the invention are suitable for preventing or treating diseases that are caused or promoted by persistent angiogenesis.

Since the compounds of formula (I) are identified as inhibitors of the tyrosine kinases VEGFR-1 and VEGFR-2, they are suitable in particular for preventing or treating those diseases that are caused or promoted by persistent angiogenesis that is triggered via the VEGF receptor or by an increase in vascular permeability.

The present invention also provides the use of the compounds of formula (I) as inhibitors of the tyrosine kinases VEGFR-1 and VEGFR-2, or KDR and FLT.

The term "diseases that are caused or promoted by persistent angiogenesis" relates especially to diseases such as tumor or metastasis growth, psoriasis, Kaposi's sarcoma, restenosis, such as, e.g., stent-induced restenosis, endometriosis, Crohn's disease, Hodgkin's disease, leukemia; arthritis, such as rheumatoid arthritis, hemangioma, angiofibroma; eye diseases, such as diabetic retinopathy, neovascular glaucoma; corneal transplants; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases, arteriosclerosis, injuries to nerve tissue, and for inhibiting the reocclusion of vessels after balloon catheter treatment, in vascular prosthetics or after mechanical devices are used to keep vessels open, such as, e.g., stents, as immunosuppressive agents, for supporting scar-free healing, in senile keratosis, in contact dermatitis, and in asthma.

In treating injuries to nerve tissue, quick scar formation on the injury sites can be prevented with the compounds according to the invention, i.e., scar formation is prevented from occurring before the axons reconnect. A reconstruction of the nerve compounds can be thus facilitated.

The formation of ascites in patients, especially patients suffering from tumors caused by metastases, can also be suppressed with the compounds according to the invention. VEGF-induced oedemas can also be suppressed.

By a treatment with the compounds of formula (I), not only a reduction of the size of metastases but also a reduction of the number of metastases can be achieved.

Lymphangiogenesis plays an important role in lymphogenic metastasis (Karpanen, T. et al., Cancer Res. 2001 Mar. 1, 61(5): 1786-90, Veikkola, T., et al., EMBO J. 2001, Mar. 15; 20 (6): 1223-31).

The compounds of formula (I) also show excellent action as VEGFR kinase 3 inhibitors and are, therefore, also suitable as effective inhibitors of lymphangiogenesis.

The compounds of formula (I) are thus effective in the prevention or treatment of diseases that are associated with excessive lymphangiogenesis, such as lymphedema, lymphangiectasia, lymphangioma, and lymphangiosarcoma but also asthma. Lymphatic growth around tumors may facilitate metastatic spread of malignant cells that ultimately kill the patient. This process can be effectively hindered by the compounds of this invention. Thus the compounds are not only effective in inhibiting metastasis growth, but can also be effective in reducing the number of metastases.

This invention also provides the use of the compounds of formula (I) as inhibitors of the tyrosine kinase VEGFR-3 (FLT-4).

A further object of this invention is also a pharmaceutical agent for preventing or treating diseases that are associated with excessive lymphangiogenesis, such as metastasis growth, lymphedema, lymphangiectasia, lymphangioma, and lymphangiosarcoma but also asthma.

Furthermore, the invention relates to the use of the compounds of general formula (1) for the preparation of a pharmaceutical agent for use in or for the prevention or treatment of tumor or metastasis growth, psoriasis, Kaposi's sarcoma, restenosis, such as, e.g., stent-induced restenosis, endometriosis, Crohn's disease, Hodgkin's disease, leukemia; arthritis, such as rheumatoid arthritis, hemangioma, angiofibroma; eye diseases, such as diabetic retinopathy, neovascular glaucoma; corneal transplants; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases, arteriosclerosis, injuries to nerve tissue, and for inhibiting the reocclusion of vessels after balloon catheter treatment, in vascular prosthetics or after mechanical devices are used to keep vessels open, such as, e.g., stents, as immunosuppressive agents, for supporting scar-free healing, in senile keratosis, in contact dermatitis, and also in asthma.

To use the compounds of formula (I) as pharmaceutical agents, the latter are brought into the form of a pharmaceutical preparation, which in addition to the active ingredient for enteral or parenteral administration contains suitable pharmaceutical, organic or inorganic inert carrier materials, such as, for example, water, gelatin, gum arabic, lactose, starch, magnesium stearate, talc, vegetable oils, polyalkylene glycols, etc. The pharmaceutical preparations can be present in solid form, for example as tablets, coated tablets, suppositories, capsules or in liquid form, for example as solutions, suspensions or emulsions. They also can contain, moreover, adjuvants such as preservatives, stabilizers, wetting agents or emulsifiers, salts for changing osmotic pressure or buffers.

For parenteral administration, especially injection solutions or suspensions, especially aqueous solutions of the active compounds in polyhydroxyethoxylated castor oil, are suitable.

As carrier systems, surface-active adjuvants such as salts of bile acids or animal or plant phospholipids, but also mixtures thereof as well as liposomes or components thereof can also be used.

For oral administration, especially tablets, coated tablets or capsules with talc and/or hydrocarbon vehicles or binders, such as for example, lactose, corn starch or potato starch, are suitable. The administration can also be carried out in liquid form, such as, for example, as juice, to which optionally a sweetener or, if necessary, one or more flavouring substances, is added.

The dosage of the active ingredients can vary depending on the method of administration, age and weight of the patient, type and severity of the disease to be treated and similar factors. The daily dose is 0.5-1000 mg, preferably 50-200 mg, whereby the dose can be given as a single dose to be administered once or divided into 2 or more daily doses.

A further object of this invention is therefore a pharmaceutical agent comprising a compound of formula (I) in combination with at least one pharmaceutically acceptable carrier or excipient.

Compounds of formula (I) are obtained, in that a compound of general formula (II):

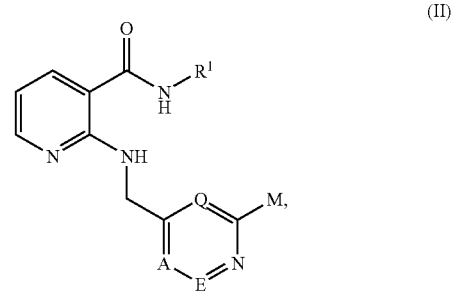

in which A, E, Q, and $R^1$ are defined supra as for general formula (I) and M stands for halogen, is (i) first converted to an amine and then, by reaction with a carbamoyl chloride of formula $ClCONR^2R^3$ in which $R^2$ and $R^3$ are defined supra as for general formula (I), is converted to a urea of general formula (I), or (ii) reacted with a urea of general formula $R^9HNCONR^2R^3$ in which $R^2$, $R^3$ and $R^9$ are defined supra as for general formula (I), or (iii) first converted to an amine, then converted to a compound of formula (I) by first reacting with a compound of formula $ClCO_2Ph$ and then reacting with a compound of formula $HNR^2R^3$, wherein $R^2$ and $R^3$ are defined supra as for general formula (I); or a compound of general formula (III) in which A, E, Q, $R^2$, $R^3$ and $R^9$ are defined as for general formula (I) and $R^Y$ stands for H or $C_1$-$C_6$-alkyl, is reacted with an amine of general formula $R^1NH_2$ in which $R^1$ is defined supra as for general formula (I):

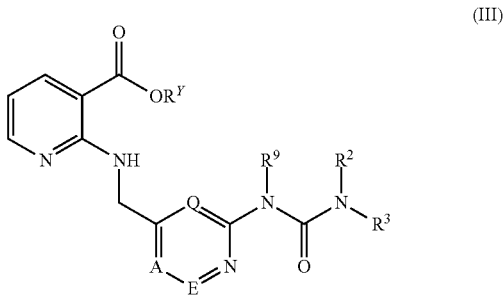

(III)

There are many methods known to the person skilled in the art in the literature for amide formation. For example, it is possible to start from the corresponding ester. The ester may be reacted according to J. Org. Chem. 1995, 8414 with trimethylaluminium and the corresponding amine in solvents such as toluene, at temperatures of 0° C. to the boiling point of the solvent. If the molecule contains two ester groups, both are converted into the same amide. Instead of trimethylaluminium, sodium hexamethyldisilazide can also be used.

For amide formation, however, all processes that are known to the person skilled in the art from peptide chemistry are also available. For example, the corresponding acid, obtained from the corresponding ester by saponification, can be reacted with the amine in aprotic polar solvents, such as, for example, dimethylformamide, via an activated acid derivative, obtainable, for example, with hydroxybenzotriazole and a carbodiimide, such as, for example, diisopropylcarbodiimide, at temperatures of between 0° C. and the boiling point of the solvent, preferably at 80° C., or else with preformed reagents, such as, for example, HATU (O-(7-azabenzotriazol-1-yl)-1,1,3,3-tetramethyluronium hexafluorophosphate) (Chem. Comm. 1994, 201), at temperatures of between 0° C. and the boiling point of the solvent, preferably at room temperature. The addition of a base such as N-methylmorpholine, for example, is necessary. Amide formation, may also be accomplished via the acid halide, mixed acid anhydride, imidazolide or azide.

The ureas of aryl- or heteroaryl amines may be prepared by a variety of literature known methods, known to the person skilled in the art. For example, they may be prepared by the reaction of aryl- or heteroaryl amines with isocyanates, the reaction of amines with aryl- or heteroaryl-carbamates such as aryl- or heteroaryl-phenoxycarbamates, or the reaction of aryl- or heteroaryl amines with appropriately substituted carbamoyl chlorides, or the reaction of an aryl- or heteroaryl-halide with ureas under the influence of metal catalysis.

For example, the ureas of aminopyridines may be prepared by reacting a urea with halopyridines, whereby chloro and bromopyridines are preferred, under the catalytic influence of metal complexes, for example, palladium- or copper complexes. In the case of copper complexes the use of stoichiometric amounts of the copper complexes may be advantageous for the reaction outcome. Suitable copper salts for the reaction are copper (I) or copper (II) salts whereby copper (I) salts such as, for example, copper (I) oxide or copper (I) iodide, are preferred. In the case of copper (I) iodide the addition of an additive such as, for example, ethylenediamine is necessary. Suitable solvents for this copper-promoted coupling are dioxane or dimethylformamide, at temperatures upto the boiling point of the solvents, whereby 120° C. is preferred. Addition of a base is also necessary, such as potassium phosphate or cesium carbonate. In the case of palladium catalysis, palladium complexes such as tris-(dibenzylideneacetone)-dipalladium(0) maybe employed. Suitable solvents for the reaction are toluene, dioxane or dimethylformamide, whereby mixtures of solvents may also be advantageous for the reaction, at temperatures from room temperature to the boiling points of the solvents, whereby 110° C. is preferred. A co-ligand such as BINAP, DPPF or xantphos is also employed. A base is also required, suitable bases for the reaction are for example, cesium carbonate, potassium phosphate or sodium tert-butoxide.

The required urea starting materials for the above copper or palladium promoted coupling may in turn be prepared from the reaction of the corresponding amines with the corresponding isocyanates. Solvents such as for example dichloromethane, or isopropylalcohol may be employed at temperatures from 0° C. to the boiling points of the solvents, whereby room temperature is preferred.

The required 2-amino-nicotinic acid esters (general formula II, Scheme 1) may be prepared by a variety of methods. For example, known 2-chloronicotinic acid esters may be reacted with appropriately substituted amines at elevated temperatures whereby 120° C. is preferred. The reaction may be conducted without solvents. In turn, the amines may be obtained from the corresponding nitrites, for example, by hydrogenation in the presence of a suitable metal catalyst, such as Raney Nickel. Alternatively, the nitrile may be reduced with metal hydride reagents such as, for example, lithium aluminium hydride. Similar reductions of aryl nitrites to benzylamines are well documented in the literature and are well known to the person skilled in the art. An alternative preparation of the required 2-amino-nicotinic acid esters is accomplished as outlined in Scheme 1, in which A, E, Q, $R^1$, $R^2$, $R^3$, and $R^9$ are defined in the same way as for the general formula (I), M is halogen and $R^Y$ is H or $C_1$-$C_6$-alkyl. Esterification of 2-aminonicotinic acid may be accomplished by a variety of well known techniques, well known to the person skilled in the art. Acylation with an appropriately substituted activated acid derivative, for example, the corresponding acid halides or anhydrides, whereby the acid chloride is preferred, in inert solvents, for example, dichloromethane, with addition of tertiary amine bases, for example triethylamine, with cooling, whereby cooling at 0° C. is preferred, delivers the corresponding amide derivatives. The amides may be reduced to compounds of general formula (II) by employing a suitable reducing agent, for example a borane complex such as borane-dimethyl sulphide complex, in solvents, for example, tetrahydofuran, at temperatures ranging from chilled to room temperature to the boiling point of the solvents, whereby room temperature is preferred.

Scheme 1

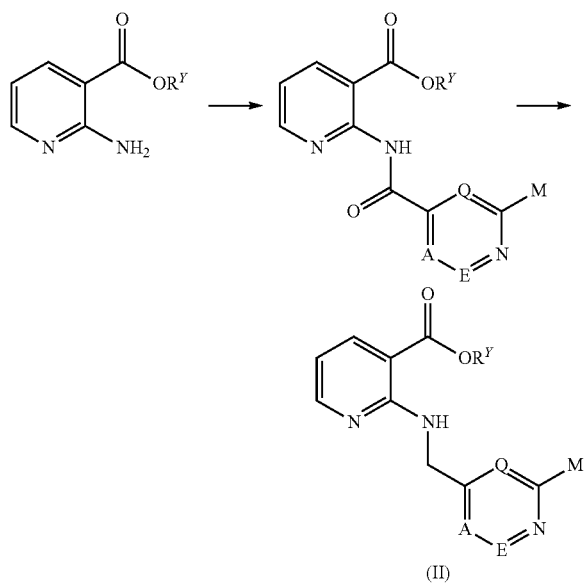

Methods for the preparation of substituted or unsubstituted 6-aminoindazoles are well known to the person skilled in the art, in the literature. They may be obtained from the reduction of the corresponding nitroindazoles via catalytic hydrogenation or other reduction methods well known to the person skilled in the art. N-alkylation of substituted nitroindazoles may be accomplished with a variety of literature-known alkylating agents. For example, methylation of N-1 or N-2 of a suitably functionalised 6-nitroindazole may be accomplished by for example treatment with a base, preferably $Cs_2CO_3$ or NaH, and a methyl halide, preferably methyl iodide in a suitable solvent such as N,N-dimethylformamide, at temperatures ranging from 0° C. to 50° C., whereby 50° C. is preferred. 3-Substituted-6-nitroindazoles may be prepared by a variety of methods. For example alkyl substituents may be introduced in the 3-position by way of standard Suzuki reactions between an appropriate 3-haloindazole, whereby the appropriate 3-iodoindazoles are preferred, and an alkyl boronic acid, whereby the trialkylboraxines may also be employed. N-protection of the indazole may be advantageous for the reaction. 6-Nitroindazole-3-carboxylic acid provides a suitable starting material for ester, amide, hydroxymethyl and alkoxymethyl substitution in the 3-position of 6-nitroindazole, via transformations well known to the person skilled in the art, such as transesterification, amide coupling, reduction, or reduction followed by alkylation. 6-Nitroindazole-3-carbaldehyde (prepared by the reaction of commercial 6-nitroindole with $NaNO_2$ in the presence of dilute aqueous hydrochloric acid according to J. Med. Chem. 2001, 44, 7, 1021) provides a useful precursor to 6-nitroindazole-3-carboxylic acid via well known oxidation methods. In turn 6-nitroindazole-3-carbaldehyde may also be converted to 3-hydroxymethyl-6-nitroindazole, 3-alkoxymethyl-6-nitroindazole, or 3-aminomethyl-6-nitroindazole derivatives by equally standard transformations such as reduction, reduction followed by alkylation, or reductive amination. Such standard transformations may also be applied to the synthesis of other substituted aminoindazoles. A variety of substituted nitroindazoles are commercially available, however they may be readily synthesised via the reaction of a suitable 2-aminonitrotoluene derivative with, for example, $NaNO_2$ and aqueous hydrochloric acid. If required, the nitro group may be introduced after the cyclisation reaction of a suitable 2-aminotoluene derivative by standard nitration chemistry.

The preparation of N-alkylated-aminobenzimidazoles may be accomplished from the corresponding N-alkylated-nitrobenzimidazoles via standard reduction chemistry. Alkylation of a suitable functionalised nitrobenzimidazole, for example with an alkyl halide and a base, furnishes N1- and N3-alkylated-nitrobenzimidazoles, which may be separated and isolated in pure form by standard purification techniques. For example, 6-amino-1-methyl-benzimidazole may be produced by the reaction of commercial 5-nitrobenzimidazole with MeI and $Cs_2CO_3$ in DMF followed by purification (of the resulting mixture of 5- and 6-nitro-1-methyl-benzimidazoles) and hydrogenation in the presence of 10% Pd on charcoal. Similarly, the preparation of N-alkylated-aminobenzotriazoles may also be accomplished from the corresponding nitrobenzotriazoles. Alkylation of a suitable functionalised nitrobenzotriazole, for example with an alkyl halide and a base, furnishes N1-, N2- and N3-alkylated-nitrobenzotriazoles, which may be separated and isolated in pure form by standard purification techniques. Standard reduction chemistry furnishes the corresponding aminobenzotriazoles. For example, 5-amino-2-methyl-benzotriazole may be prepared according to a literature procedure (Eur. J. Med. Chem. 1992, 27, 161-166).

The preparation of 3-aminoisoquinolines which are substituted in the 7-position, may be accomplished via the corresponding 3-amino-1-bromo-7-substituted isoquinoline by way of reductive dehalogenation. 3-amino-1-bromo-7-substituted isoquinolines may in turn be prepared by the reaction of a suitable 2-cyano-4-substituted-benzeneacetonitrile with HBr in acetic acid. For example, 3-amino-7-methoxyisoquinoline may be prepared in two steps (HBr mediated cyclisation followed by reductive dehalogenation) from 2-cyano-4-methoxy-benzeneacetonitrile, which may be prepared according to a literature procedure (Bull. Chem. Soc. Jpn. 1980, 53, 10, 2885-2890).

1-Alkyl-6-amino-quinolin-2-ones may be prepared by methods known to the person skilled in the art. For example, 6-amino-2-methyl-quinolin-2-one may be prepared according to a literature procedure (J. Chem. Research, Synopses, 1997, 310-311).

2-Amino-3,6-disubstituted quinolines may be prepared by a number of procedures. For example, the reaction of the lithium salt (generated with a base such as lithium diisopropylamide) of a suitably substituted cyanomethyl-dialkylphosphonate with a suitably substituted 2-nitrobenzaldehyde derivative in a suitable solvent, such as THF, furnishes a suitable acrylonitrile derivative which may be cyclised to the desired 2-amino-3,6-disubstituted quinoline by treating with a suitable reducing agent, such as iron in acetic acid.

The compounds of the general formulae II, III, and IIIA:

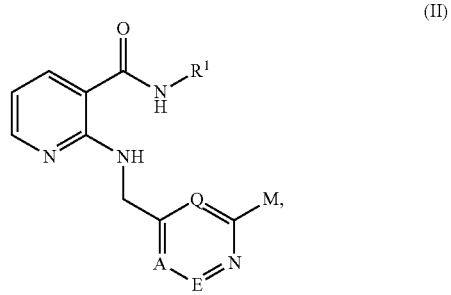

-continued

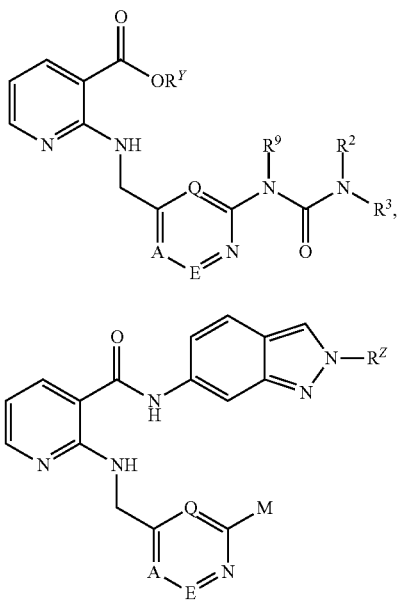

in which A, E, Q, $R^1$, $R^2$, $R^3$, and $R^9$ are defined in the same way as for the general formula (I), $R^Z$ is $C_1$-$C_{12}$-alkyl, M is halogen and $R^Y$ is H or $C_1$-$C_6$-alkyl, provide valuable intermediates for the preparation of the inventive compounds of general formula (I) and, are therefore also objects of the invention. The use of compounds of formula (II) and (III) in the production of a compound of formula (I), as well as the process described above using these compounds in the production of a compound of formula (I) are also objects of the invention.

EXAMPLES

Production of the Compounds According to the Invention

The following examples explain the production of the compounds according to the invention without the scope of the claimed compounds being limited to these examples.

Abbreviations

The following abbreviations used in the invention have the following meanings:

| | |
|---|---|
| Brine | saturated aqueous sodium chloride solution |
| CI+ | chemical ionisation (NH₃) |
| DCE | 1,2-dichloroethane |
| DMF | N,N-dimethyl formamide |
| d₆-DMSO | d₆-dimethylsulphoxide |
| d | doublet |
| dd | doublet of doublets |
| ES+ | positive mode electrospray ionisation |
| EtOAc | ethyl acetate |
| EtOH | ethanol |
| 1H-NMR | proton nuclear magnetic resonance spectroscopy: chemical shifts (δ) are given in ppm. |
| Hex | n-hexane |
| LC-ES+ | liquid chromatography/positive mode electrospray ionisation |
| LDA | Lithium diisopropylamide |
| MeOH | methanol |
| m | multiplet |
| Mp. | melting point |
| MS | mass spectrometry |
| m/z | mass/charge ratio |
| Pd₂dba₃ | tris-(dibenzylideneacetone)-dipalladium(0)-chloroform complex |
| rt | room temperature |
| RT | retention time (LC) |
| s | singlet |
| THF | tetrahydrofuran |
| t | triplet |
| Xantphos | 9,9-dimethyl-4,5-bis(diphenylphosphino)xanthene |

Example 1.0

Preparation of N-(2-methyl-2H-indazol-6-yl)-2-{[2-(3-methyl-ureido)-pyridin-4-ylmethyl]-amino}-nicotinamide

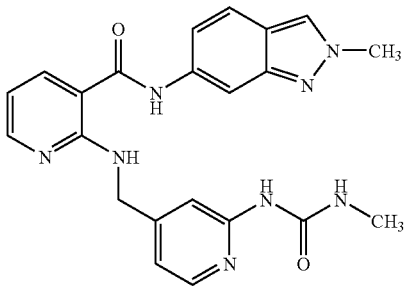

A suspension of 2-methyl-2H-indazol-6-ylamine [Davies *J. Chem. Soc.*; 1955; 2412-2419] (809 mg, 5.5 mmol) in DCE (13.5 mL) was treated at 0° C. consecutively with, trimethylaluminium (2 M) in toluene (4.23 mL, 8.46 mmol), 2-{[2-(3-methyl-ureido)-pyridin-4-ylmethyl]-amino}-nicotinic acid methyl ester (1.34 g, 4.23 mmol) and DCE (20 mL). The reaction mixture was placed under a nitrogen atmosphere and heated for 10 hours at 85° C. (bath temperature). On cooling the reaction was poured into aqueous sodium-potassium tartrate solution (150 mL) and partitioned between EtOAc and water. The organic phase was washed with brine, dried, filtered and concentrated in vacuo. The residue was purified by chromatography on silica gel (Gradient elution: 100% CH₂Cl₂ to 90% CH₂Cl₂/10% MeOH) to give N-(2-methyl-2H-indazol-6-yl)-2-{[2-(3-methyl-ureido)-pyridin-4-ylmethyl]-amino}-nicotinamide (964 mg, 53%) as a solid; Mp. 205-207° C.

The following examples were prepared in analogy to Example 1 from 2-{[2-(3-methyl-ureido)-pyridin-4-ylmethyl]-amino}-nicotinic acid methyl ester and the corresponding amine:

| Example Nr. | R¹ | MW | Mp. [° C.] |
|---|---|---|---|
| 1.1 | 3-(trifluoromethyl)phenyl | 444.42 | 206-207 |
| 1.2 | 1-methyl-1H-indazol-6-yl | 430.47 | 228-229 |
| 1.3 | isoquinolin-3-yl | 427.47 | 191-192 |
| 1.4 | 1-methyl-1H-indazol-5-yl | 430.47 | 219-220 |

Example 2.0

Preparation of morpholine-4-carboxylic acid (4-{[3-(2-methyl-2H-indazol-6-ylcarbamoyl)-pyridin-2-ylamino]-methyl}-pyridin-2-yl)-amide

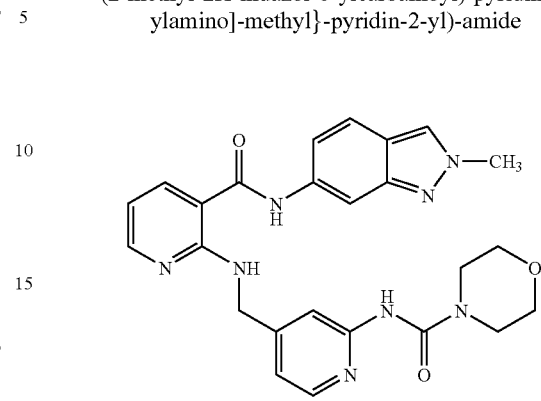

A mixture of 2-[(2-chloro-pyridin-4-ylmethyl)-amino]-N-(2-methyl-2H-indazol-6-yl)-nicotinamide (200 mg, 0.51 mmol), $Pd_2 dba_3$ (5.2 mg, 0.0051 mmol), xantphos (9.1 mg, 0.0153 mmol), cesium carbonate (169 mg, 0.54 mmol) and morpholine-4-carboxylic acid amide (332 mg, 2.55 mmol) in dioxane (12.1 mL) and DMF (4.1 mL) under nitrogen, was stirred at 110° C. for 11 hours. A second reaction was performed in duplicate. The two reactions were combined, diluted with dilute aqueous sodium hydrogencarbonate solution and extracted with EtOAc. The combined organic layers were washed with brine, dried and concentrated in vacuo. Purification was achieved by chromatography on Isolute® flash silica gel (Separtis) to give morpholine-4-carboxylic acid (4-{[3-(2-methyl-2H-indazol-6-ylcarbamoyl)-pyridin-2-ylamino]-methyl}-pyridin-2-yl)-amide (119 mg) which was further purified by recrystallisation from EtOAc; 1H-NMR (300 MHz, $d_6$-DMSO) 10.2 (1H, s), 9.06 (1H, s), 8.45 (1H, t), 8.22 (1H, s), 8.03-8.13 (4H, m), 7.73 (1H, s), 7.62 (1H, d), 7.27 (1H, unresolved dd), 6.89 (1H, unresolved dd), 6.67 (1H, dd), 4.62 (2H, d), 4.10 (3H, s), 3.52 (4H, t), 3.39 (4H, t).

The following examples were prepared in analogy to Example 2.0 from the corresponding 2-chloropyridine derivative and the corresponding urea:

| Example Nr. | Structure | MW | H-NMR ($d_6$-DMSO) |
|---|---|---|---|
| 2.1 | (N,N-dimethylurea derivative) | 444.50 | δ (600 MHz) 10.25 (1H, s), 8.74 (1H, s), 8.48 (1H, t), 8.27 (1H, s), 8.15-8.17 (1H, m), 8.08-8.13 (3H, m), 7.77 (1H, s), 7.65 (1H, d), 7.29 (1H, d), 6.90 (1H, d), 6.69 (1H, dd), 4.65 (2H, d), 4.14 (3H, s), 2.91 (6H, s). |

| Example Nr. | Structure | MW | H-NMR (d6-DMSO) |
|---|---|---|---|
| 2.2 | 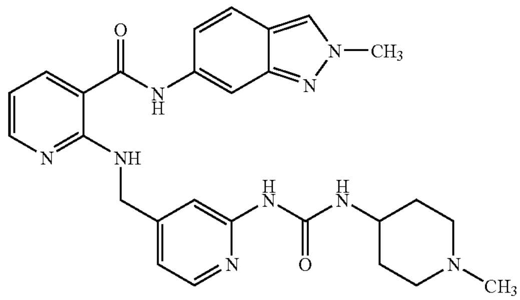 | 513.60 | δ (600 MHz) 10.22 (1H, s), 9.06 (1H, s), 8.50 (1H, t), 8.25 (1H, s), 8.05-8.17 (4H, m), 7.65 (1H, d), 7.37-7.40 (1H, m), 7.27-7.31 (1H, m), 6.85 (1H, d), 6.69 (1H, dd), 4.62 (2H, d), 4.13 (3H, s), 3.49-3.57 (1H, m), 2.58-2.65 (2H, m), 2.17 (3H, s), 2.02-2.11 (2H, m), 1.78-1.83 (2H, m), 1.37-1.46 (2H, m). |
| 2.3 | 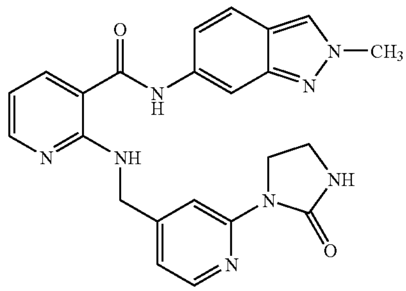 | 442.48 | δ (300 MHz) 10.23 (1H, s), 8.49 (1H t), 8.27 (1H, s), 8.09-8.19 (5H, m), 7.65 (1H, d), 7.30 (1H, unresolved dd), 7.11 (1H, s), 6.92 (1H, d), 6.69 (1H, dd), 4.65 (2H, d), 4.12 (3H, s), 3.97 (2H, t), 3.38 (2H, t). |

Production of Starting and Intermediate Compounds

If the production of the intermediate compounds is not described, the latter are known or can be produced analogously to known compounds or processes that are described here or in WO2004/013102.

Example 3.1

Preparation of 1-(4-cyano-pyridin-2-yl)-3-methyl-urea

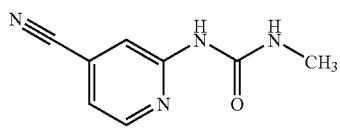

A mixture of 2-chloro-isonicotinonitrile [Talik et al. *Rocz. Chem.;* 29; 1955; 1019, 1025.] (13.9 g, 0.1 mol), Pd₂dba₃ (2.0 g, 2 mmol), Xantphos (3.6 g, 6.22 mmol), cesium carbonate (39.1 g, 120 mmol) and methylurea (37.04 g, 0.5 mol) in dioxane (800 mL), under a nitrogen atmosphere was heated for 8 hours at 130° C. (bath temperature). On cooling the reaction mixture was concentrated in vacuo. The residue was partitioned between CH₂Cl₂ and water. The organic phase was washed with brine, dried, filtered and concentrated in vacuo. The residue was purified by chromatography on silica gel (gradient elution: 100% hexane to 100% EtOAc) to give 1-(4-cyano-pyridin-2-yl)-3-methyl-urea (12.1 g) as a solid; Mp. 203-204° C.

Example 3.2

Preparation of 1-(4-aminomethyl-pyridin-2-yl)-3-methyl-urea

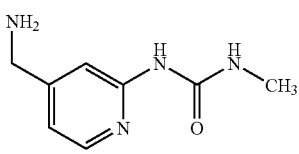

A solution of 1-(4-cyano-pyridin-2-yl)-3-methyl-urea (12.0 g, 11.4 mmol) in THF (80 mL) was treated with Raney nickel (0.5 g) placed under a hydrogen atmosphere (atmospheric pressure) for 8 hours at rt. The reaction mixture was diluted with EtOAc, filtered over Celite® and concentrated in vacuo. The residue was purified by chromatography on silica gel (Gradient elution: 100% CH₂Cl₂ to 85%/15% CH₂Cl₂/MeOH) to give 1-(4-aminomethyl-pyridin-2-yl)-3-methyl-urea (4.8 g) as a solid.

Example 3.3

Preparation of 2-{[2-(3-methyl-ureido)-pyridin-4-ylmethyl]-amino}-nicotinic acid methyl ester

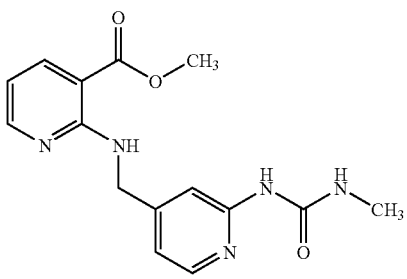

A mixture of 1-(4-aminomethyl-pyridin-2-yl)-3-methyl-urea (3.8 g, 21.1 mmol) and 2-chloro-nicotinic acid methyl ester [Mann et al. *J. Chem. Soc.;* 1952; 2057, 2060] (1.78 g, 10.4 mmol) was heated for 1 hour at 120° C. The crude product was purified by chromatography on silica gel (Gradient elution: 100% CH$_2$Cl$_2$ to 93% CH$_2$Cl$_2$/7% MeOH) to give 2-{[2-(3-methyl-ureido)-pyridin-4-ylmethyl]-amino}-nicotinic acid methyl ester (2.06 g); Mp. 145-146° C.

Example 4.1

Preparation of 2-amino-nicotinic acid methyl ester

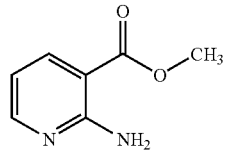

A stirred suspension of 2-amino-nicotinic acid (12.15 g, 87.95 mmol) in a mixture of MeOH (175 mL) and THF (500 mL), under nitrogen at room temperature, was added a solution of trimethylsilyldiazomethane (2M in hexane, 50 mL, 99.5 mmol)) dropwise. After completion of the reaction the volatiles were removed in vacuo and the crude product triturated with disisopropyl ether, filtered and dried to give 2-amino-nicotinic acid methyl ester (10.44 g) as a yellow solid.

Example 4.2

Preparation of 2-chloro-isonicotinoyl chloride

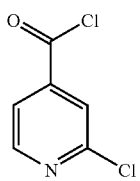

A mixture of 2-chloro-isonicotinic acid (15 g, 95.2 mmol) and thionyl chloride (90 mL) was heated at 100° C. After completion of the reaction the mixture was concentrated in vacuo. Residual thionyl chloride was removed by azeotropic distillation with toluene, to give 2-chloro-isonicotinoyl chloride (15.33 g).

Example 4.3

Preparation of 2-[(2-chloro-pyridine-4-carbonyl)-amino]-nicotinic acid methyl ester

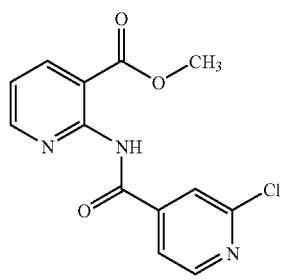

A stirred and chilled (0° C.) mixture of 2-amino-nicotinic acid methyl ester (11 g, 72.3 mmol) in dichloromethane was treated sequentially with triethylamine (11 mL, 79.5 mmol) and a solution of 2-chloro-isonicotinoyl chloride (12.73 g, 72.3 mmol) in dichloromethane, such that the total volume of solvent was 80 mL. The reaction was warmed to room temperature and on completion of the reaction was quenched by addition of water. The aqueous phase was separated and extracted with EtOAc. The combined organic phases were washed with brine, dried and concentrated in vacuo. The residue was suspended in hot hexane, filtered while hot and the resulting solid recrystallised from EtOH, to give 2-[(2-chloro-pyridine-4-carbonyl)-amino]-nicotinic acid methyl ester (12.76 g); 1H-NMR (300 MHz, d$_6$-DMSO) 11.47 (1H, s), 8.62-8.67 (2H, m), 8.20 (1H, unresolved dd), 7.99 (1H, s), 7.89 (1H, unresolved dd), 7.43 (1H, dd), 3.72 (3H, s).

Example 4.4

Preparation of 2-[(2-chloro-pyridin-4-ylmethyl)-amino]-nicotinic acid methyl ester

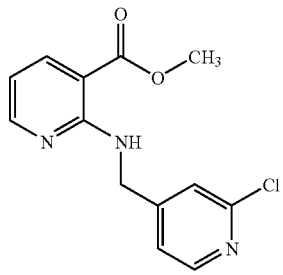

A stirred solution of 2-[(2-chloro-pyridine-4-carbonyl)-amino]-nicotinic acid methyl ester (4 g, 13.72 mmol) in dry THF (60 mL), under nitrogen, was treated with borane-dimethyl sulphide complex (2M solution in THF, 34 mL, 68.6 mmol). On completion of the reaction the mixture was carefully poured into MeOH and the resulting mixture heated at reflux for 30 minutes. The volatiles were removed in vacuo and the residue partitioned between dilute aqueous sodium hydrogencarbonate solution and dichloromethane. The aqueous layer was extracted with dichloromethane and the combined organic layers washed with brine, dried and concentrated in vacuo. Purification was achieved by chromatography on Isolute® flash silica gel (Separtis) to give 2-[(2-chloro-pyridin-4-ylmethylamino]-nicotinic acid methyl ester (0.76 g); 1H-NMR (300 MHz, d$_6$-DMSO) 8.47 (1H, t), 8.30 (1H, d), 8.23 (1H, unresolved dd), 8.13 (1H, unresolved dd), 7.38 (1H, s), 7.30 (1H, d), 6.68 (1H, dd), 4.73 (2H, d), 3.85 (3H, s).

Example 4.4

Preparation of 2-[(2-chloro-pyridin-4-ylmethyl)-amino]-N-(2-methyl-2H-indazol-6-yl)-nicotinamide

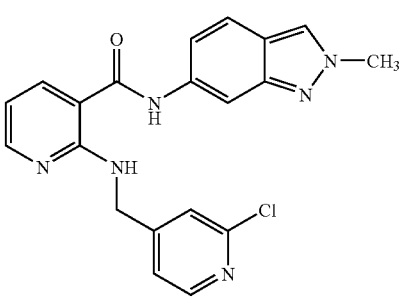

To a stirred and chilled (0° C.) suspension of 2-methyl-2H-indazol-6-ylamine (1.52 g) in DCE (6 mL), under nitrogen, was added trimethylaluminium (2M solution in toluene, 5 mL, 9.37 mmol). This mixture was added dropwise to a stirred and chilled (0° C.) solution of 2-[(2-chloro-pyridin-4-ylmethyl)-amino]-nicotinic acid methyl ester (1.45 g, 5.21 mmol) in DCE (14.7 mL). The mixture was heated at 100° C. for 2 hours before cooling to room temperature and quenching by pouring into aqueous sodium-potassium tartrate solution. The mixture was extracted with EtOAc and the combined organic layers washed successively with dilute aqueous citric acid solution, dilute aqueous sodium hydrogen carbonate solution and brine, dried and concentrated in vacuo to give 2-[(2-chloro-pyridin-4-ylmethyl)-amino]-N-(2-methyl-2H-indazol-6-yl)-nicotinamide (1.58 g); $^1$H-NMR (300 MHz, $d_6$-DMSO) 10.26 (1H, s), 8.40 (1H, t), 8.28 (1H, d), 8.25 (1H, s), 8.06-8.12 (3H, m), 7.62 (1H, d), 7.35 (1H, s), 7.30 (1H, unresolved dd), 7.27 (1H, unresolved dd), 6.68 (1H, dd), 4.67 (2H, d), 4.10 (3H, s).

Example 5.0

Preparation of morpholine-4-carboxylic acid amide

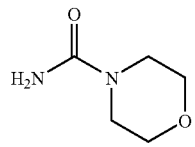

To a stirred solution of morpholine (1.3 mL, 15 mmol) in isopropanol (30 mL) at rt was added trimethylsilylisocyanate (2.8 mL, 21 mmol) and the resulting solution stirred overnight before the volatiles were removed in vacuo to give morpholine-4-carboxylic acid amide (2.0 g, quant.) as a solid; 1H-NMR (300 MHz, $d_6$-DMSO) 6.00 (2H, s), 3.51-3.54 (4H, s), 3.23-3.26 (4H, s).

Example 5.1

Preparation of (1-methyl-piperidin-4-yl)-urea

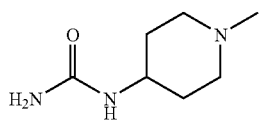

(1-methyl-piperidin-4-yl)-urea was prepared from 1-methyl-piperidin-4-ylamine and trimethylsilylisocyanate, in analogy to Example 5.0; 1H-NMR (300 MHz, $d_6$-DMSO) 5.86 (1H, d), 5.32 (2H, s), 3.21-3.38 (1H, m), 2.58-2.67 (2H, m), 2.11 (3H, s), 1.88-1.98 (2H, m), 1.65-1.72 (2H, m), 1.22-1.35 (2H, m).

The following examples detail the biological activity and use of the compounds of the invention without the scope of the claimed compounds being limited to these examples.

KDR Kinase Inhibition

Kinase activity was measured with a GST-kinase domain fusion construct of the KDR kinase according to the following protocol to obtain concentration response curves. Components were added into a microtiterplate in the following sequence: 10 µl of inhibitor in threefold final concentration [3% DMSO in buffer (40 mM Tris Cl pH 7.5; 1 mM DTT, 1 mM MnCl$_2$, 10 mM MgCl$_2$, 2.5 Promille Polyethyleneglycol 20000)] and 10 µl of substrate mixture [24 µM ATP, 24 µg/ml poly(Glu$_4$Tyr) in buffer, specific activity approx. 500 cpm/pmol $^{32}$P-γATP]. Reaction was started by adding 10 µl of enzyme preparation diluted appropriately in buffer that contains 10 µM vanadate. After incubation for exactly 10 min the reaction was stopped by adding of 10 µl stop solution (250 mM EDTA). 10 µl of the reaction mixture were transferred to phosphocellulose filters. The filters were washed in 0.1% phosphoric acid, dried before meltilex scintillator was applied (Wallac, Perkin-Elmer) and the radioactivity was counted.

VEGFR-3 Autophosphorylation

MVECs (1.5×10$^6$/well) of a low passage number were plated on collagen-G coated 48 well plates in EBM complete medium (including EGM-2, BD-Clonetech). 5 h later, medium was exchanged for EBM-2 without EGM-2 but containing 0.2% BSA (EBM meager). 12 h later medium was removed, 250 µl EBM-2 meager and the respective compound dilutions were added in 50 µl EBM-2 meager. Solutions were carefully mixed and left for 5 min at 4° C. before the addition of 200 µl EBM-2 meager containing VEGF-C (final concentration in the assay is 5 nM; Reliatech, Braunschweig). The solution was then carefully mixed and incubated for 15 min at room temperature. The medium was removed and cells were washed twice with cold PBS/2 mM vanadate. Cells were then lysed with 100 µl Duschl buffer [50 mM Hepes pH 7.2; 150 mM NaCl; 1 mM MgCl$_2$; 1.5% Triton X-100; 10 mM Na-Pyrophosphate; 100 mM Na-Fluoride; 10% glycerol+(freshly added before the experiment) 2 mM Orthovanadate and 1 tablet per 50 ml Complete (Roche # 1836145)]

For the ELISA, Fluoronic MaxiSorp—MTP plates (# 3204006 Zinser)—were coated overnight at 4° C. with Flt-4 antibody (Flt-4 (C-20) # sc-321 Santa Cruz); 1 µg/ml in coating buffer: Na$_2$CO$_3$ pH 9.6 100 µl/well). After 3× washing with washing buffer (0.1% Tween 20 in Na$_2$HPO$_4$ pH 7.4) the wells were incubated with 250 µl blocking buffer (Roti Block ⅒ from Roth, Karlsruhe for 1 h at room temperature). 3× Washing with washing buffer was followed by addition of cell lysates and incubation over night at 4° C. Then wells were washed 3×, anti-phosophotyrosine antibody coupled to HRP (16-105; UPSTATE; dilution 1/20000 in TBST+3% Top Block # 37766, Fluka) was added and incubated overnight at 4° C. Washing with washing buffer (6×) preceded the addition of BM chemoluminescence ELISA reagent # 1582950 (Roche) and measurement of luminescence.

Cytochrome P450 Inhibition

The Cytochrome P450 isoenzyme inhibition was performed according to the publication of Crespi et al. (Anal. Biochem., 1997, 248, 188-190) with use of the baculovirus/insect cell-expressed, human Cytochrome P 450 isoenzymes (2C9 and 2C19).

Selected results are presented in the following table:

| Example | IC50 KDR-Kinase (VEGFR-2) (nM) | IC50 CYP 2C9 (µM) | IC50 CYP 2C19 (µM) |
|---|---|---|---|
| 3.30 from WO 04/13102 | 10 | 0.9 | 1.7 |
| 3.40 from WO 04/13102 | 40 | 1.1 | 2.3 |

-continued

| Example | IC50 KDR-Kinase (VEGFR-2) (nM) | IC50 CYP 2C9 (μM) | IC50 CYP 2C19 (μM) |
|---|---|---|---|
| 3.41 from WO 04/13102 | 27 | 5.7 | 1.5 |
| 3.36 from WO 04/13102 | 98 | 1.2 | 9.0 |
| 1.0 | 10 | 11.7 | >30.0 |
| 2.0 | 29 | >30.0 | >30.0 |

The advantages of the compounds of the invention compared to known compounds can be readily demonstrated by the above studies.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European application No. 04090420.3 filed Nov. 3, 2004, and U.S. Provisional Application Ser. No. 60/626,918, filed Nov. 12, 2004, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula (I):

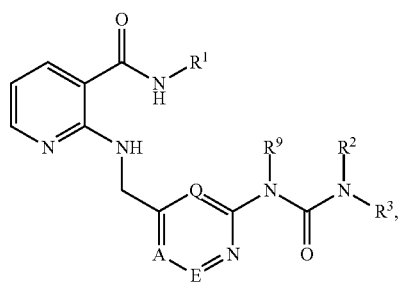

(I)

wherein:
A, E and Q independently of one another, are CH;
$R^1$ is indazolyl, which is optionally substituted in one or more places in the same way or differently with halogen, hydroxy, $C_1$-$C_{12}$-alkyl, $C_3$-$C_6$-cycloalkyl, $C_2$-$C_6$-alkenyl, $C_2$-$C_6$-alkynyl, aralkyloxy, $C_1$-$C_{12}$-alkoxy, halo-$C_1$-$C_6$-alkyl, cyano-$C_1$-$C_6$-alkyl, =O, —$SO_2R^6$, —$OR^5$, —$SOR^4$, —$COR^6$, —$CO_2R^6$ or —$NR^7R^8$, wherein $C_1$-$C_{12}$-alkyl may be substituted with —$OR^5$ or —$NR^7R^8$;

$R^2$, $R^3$ and $R^9$ independently of one another, are hydrogen or $C_1$-$C_{12}$ alkyl optionally substituted with halogen, —$OR^5$, or $C_1$-$C_{12}$-alkoxy;
$R^4$ is $C_1$-$C_{12}$-alkyl, $C_3$-$C_8$-cycloalkyl, or aryl;
$R^5$ is hydrogen, $C_1$-$C_{12}$-alkyl, $C_3$-$C_8$-cycloalkyl or halo-$C_1$-$C_6$-alkyl;
$R^6$ is hydrogen, $C_1$-$C_{12}$-alkyl, $C_3$-$C_8$-cycloalkyl, halo-$C_1$-$C_6$-alkyl, aryl, or —$NR^7R^8$; and
$R^7$ and $R^8$ independently of one another, are hydrogen, —$SO_2R^6$, —$COR^6$, aryl, $C_3$-$C_8$-cycloalkyl, $C_1$-$C_{12}$-alkyl, halo-$C_1$-$C_{12}$-alkyl, or $C_1$-$C_{12}$-alkoxy, wherein $C_1$-$C_{12}$-alkyl is optionally substituted with —$OR^5$ or —$N(CH_3)_2$, or an isomer, diastereoisomer, enantiomer, tautomer or salt thereof.

2. A compound according to claim 1, wherein $R^1$ is indazolyl substituted with $C_1$-$C_{12}$-alkyl and with a halogen atom substituent.

3. A compound according to claim 1, wherein $R^1$ is indazolyl substituted once with $C_1$-$C_{12}$-alkyl.

4. A compound according to claim 1, wherein $R^1$ is indazolyl substituted with $C_1$-$C_{12}$-alkyl.

5. A compound according to claim 1, wherein $R^1$ is indazolyl substituted with —$CH_3$.

6. A compound according to claim 1, wherein $R^1$ is 2-methyl-indazolyl.

7. A compound as claimed in claim 1, wherein $R^2$, $R^3$ and $R^9$ independently of one another, are hydrogen or $C_1$-$C_{12}$ alkyl.

8. A compound as claimed in claim 1, wherein $R^2$ and $R^3$ independently of one another, are hydrogen or —$CH_3$ and $R^9$ is hydrogen.

9. A compound according to claim 1, wherein $R^4$ is $C_1$-$C_{12}$-alkyl.

10. A compound according to claim 1, wherein $R^4$ is —$CH_3$.

11. A compound according to claim 1, wherein $R^5$ is —$CH_3$ or hydrogen.

12. A compound according to claim 1, wherein $R^5$ is hydrogen.

13. A compound according to claim 1, wherein $R^6$ is $C_1$-$C_{12}$-alkyl or —$NR^7R^8$.

14. A compound according to claim 1, wherein $R^6$ is $C_1$-$C_{12}$-alkyl.

15. A compound according to claim 1, wherein $R^6$ is —$CH_3$.

16. A compound according to claim 1, wherein $R^7$ and $R^8$ independently of one another, are hydrogen, —$COR^6$, —$SO_2R^6$, or $C_1$-$C_{12}$-alkyl.

17. A compound according to claim 1, wherein $R^7$ and $R^8$ independently of one another, are hydrogen or —$CH_3$.

18. A compound, which is selected from the group consisting of:
N-(2-methyl-2H-indazol-6-yl)-2-{[2-(3-methyl-ureido)-pyridin-4-ylmethyl]-amino}-nicotinamide,
N-(1-methyl-1H-indazol-6-yl)-2-{[2-(3-methyl-ureido)-pyridin-4-ylmethyl]-amino}-nicotinamide,
N-(1-methyl-1H-indazol-5-yl)-2-{[2-(3-methyl-ureido)-pyridin-4-ylmethyl]-amino}-nicotinamide, and
2-{[2-(3,3-dimethyl-ureido)-pyridin-4-ylmethyl]-amino}-N-(2-methyl-2H-indazol-6-yl)-nicotinamide,
and an isomer, diastereoisomer, enantiomer, tautomer and salt thereof.

19. A pharmaceutical composition comprising a compound according to claim 1 and a pharmaceutically acceptable carrier.

20. A pharmaceutical composition comprising a compound according to claim 18 and a pharmaceutically acceptable carrier.

21. A pharmaceutically acceptable salt of a compound of formula (I) according to claim 1.

22. A compound according to claim 18, which is selected from the group consisting of:

N-(2-methyl-2H-indazol-6-yl)-2-{[2-(3-methyl-ureido)-pyridin-4-ylmethyl]-amino}-nicotinamide, N-(1-methyl-1H-indazol-6-yl)-2-{[2-(3-methyl-ureido)-pyridin-4-ylmethyl]-amino}-nicotinamide, N-(1-methyl-1H-indazol-5-yl)-2-{[2-(3-methyl-ureido)-pyridin-4-ylmethyl]-amino}-nicotinamide, and 2-{[2-(3,3-dimethyl-ureido)-pyridin-4-ylmethyl]-amino}-N-(2-methyl-2H-indazol-6-yl)-nicotinamide, and a pharmaceutically acceptable salt thereof.

* * * * *